(12) United States Patent
Rothman et al.

(10) Patent No.: US 7,556,639 B2
(45) Date of Patent: *Jul. 7, 2009

(54) METHODS AND APPARATUS FOR VERTEBRAL STABILIZATION USING SLEEVED SPRINGS

(75) Inventors: Richard H. Rothman, Philadelphia, PA (US); Rafail Zubok, Midland Park, NJ (US); Mikhail Kvitnitsky, Clifton, NJ (US)

(73) Assignee: Accelerated Innovation, LLC, Clifton, NJ (US)

( * ) Notice: Subject to any disclaimer, the term of this patent is extended or adjusted under 35 U.S.C. 154(b) by 405 days.

This patent is subject to a terminal disclaimer.

(21) Appl. No.: 11/325,104

(22) Filed: Jan. 4, 2006

(65) Prior Publication Data
US 2006/0229612 A1    Oct. 12, 2006

Related U.S. Application Data

(60) Provisional application No. 60/658,365, filed on Mar. 3, 2005.

(51) Int. Cl.
A61B 17/70    (2006.01)

(52) U.S. Cl. .................................................... 606/257

(58) Field of Classification Search ................ 606/246, 606/254, 255, 257, 259, 260, 264, 265
See application file for complete search history.

(56) References Cited

U.S. PATENT DOCUMENTS

| | | | |
|---|---|---|---|
| 4,733,657 A * | 3/1988 | Kluger | 606/57 |
| 5,180,393 A | 1/1993 | Commarmond | |
| 5,672,175 A | 9/1997 | Martin | |
| 5,733,284 A | 3/1998 | Martin | |
| 6,293,949 B1 | 9/2001 | Justis | |
| 6,835,205 B2 | 12/2004 | Atkinson | |
| 6,989,011 B2 | 1/2006 | Paul et al. | |
| 2002/0026194 A1 | 2/2002 | Morrison | |
| 2003/0109880 A1 | 6/2003 | Shirado | |
| 2003/0220643 A1 * | 11/2003 | Ferree | 606/61 |
| 2004/0002708 A1 | 1/2004 | Ritland | |
| 2004/0049190 A1 | 3/2004 | Biedermann | |

(Continued)

FOREIGN PATENT DOCUMENTS

DE    10348329    2/2005

(Continued)

OTHER PUBLICATIONS

Kanayama et al, Journal of Neurosurgery 95(1 Suppl):5-10, 2001.

(Continued)

*Primary Examiner*—Eduardo C Robert
*Assistant Examiner*—Ellen Rust
(74) *Attorney, Agent, or Firm*—Matthew B. Dernier, Esq.; Gibson & Dernier LLP

(57) ABSTRACT

A stabilization element for implantation in a patient includes: a spring element including a plurality of helical coils terminating at first and second ends; and at least one sleeve including at least one bore sized and shaped to slide or thread onto the helical coils of the spring element, the at least one sleeve being operable to engage a tulip of a bone anchor.

16 Claims, 8 Drawing Sheets

U.S. PATENT DOCUMENTS

| | | |
|---|---|---|
| 2004/0236327 A1 | 11/2004 | Paul |
| 2004/0236329 A1 | 11/2004 | Panjabi |
| 2004/0267260 A1 | 12/2004 | Mack |
| 2005/0033295 A1 | 2/2005 | Wisnewski |
| 2005/0049708 A1 | 3/2005 | Atkinson |
| 2005/0056979 A1 | 3/2005 | Studer |
| 2005/0065514 A1 | 3/2005 | Studer |
| 2005/0065515 A1 | 3/2005 | Jahng |
| 2005/0065516 A1 | 3/2005 | Jahng |
| 2005/0085815 A1 | 4/2005 | Harms et al. |
| 2005/0149020 A1 | 7/2005 | Jahng |
| 2005/0154390 A1 * | 7/2005 | Biedermann et al. .......... 606/61 |
| 2005/0203519 A1 | 9/2005 | Harms et al. |
| 2006/0142758 A1 * | 6/2006 | Petit ........................... 606/61 |

FOREIGN PATENT DOCUMENTS

| | | | |
|---|---|---|---|
| DE | 102004018621 A1 * | 11/2005 | |
| EP | 1080692 A1 * | 3/2001 | |
| FR | 2806615 A1 * | 9/2001 | |
| GB | 2382304 A | 5/2003 | |
| WO | WO 9631167 A1 * | 10/1996 | |

OTHER PUBLICATIONS

Markwalder & Wenger, Acta Neurochrgica 145(3):209-14.
Stoll et al, European Spine Journal 11 Suppl 2:S170-8, 2002.
Schmoelz et al, J of spinal disorder & techniques 16(4):418-23, 2003.
International Preliminary Report on Patentability for International Application PCT/US2006001698.

* cited by examiner

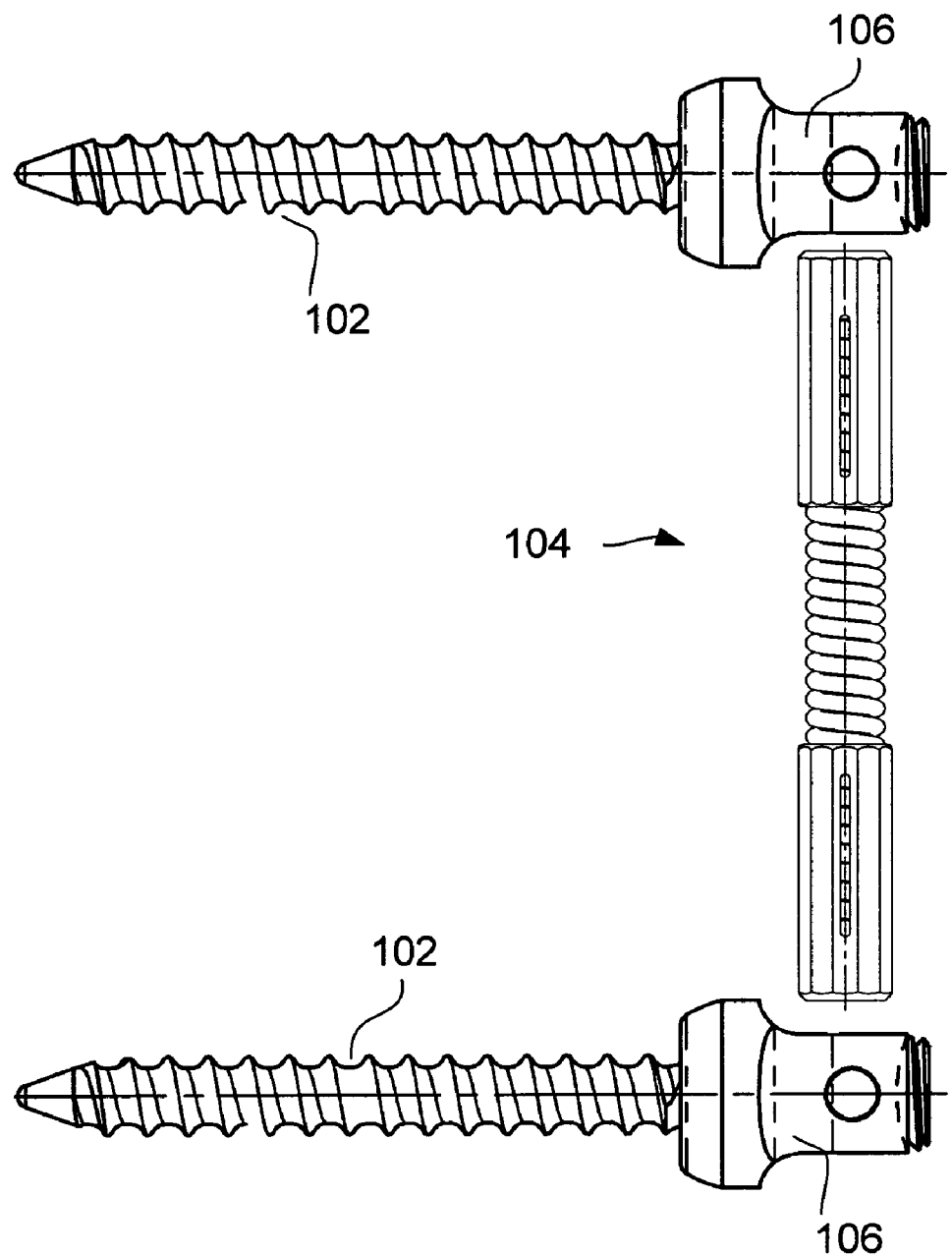

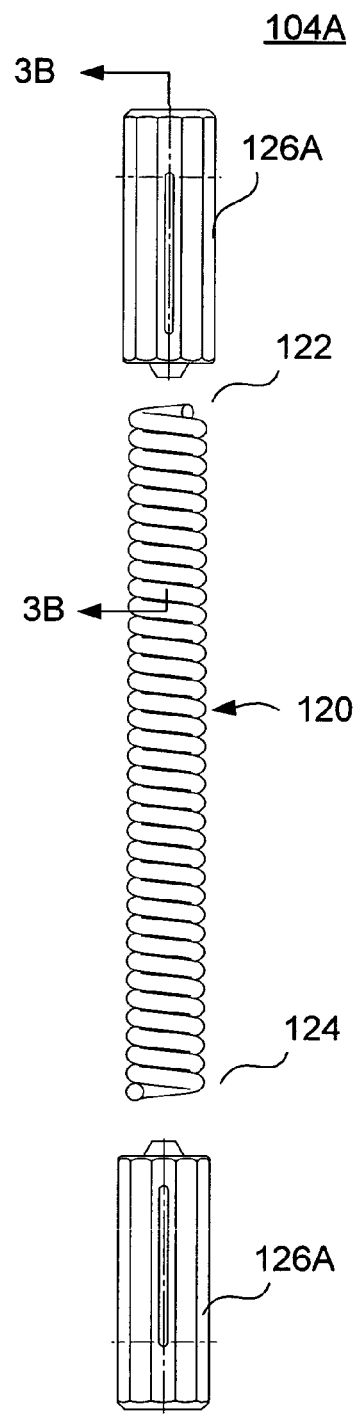
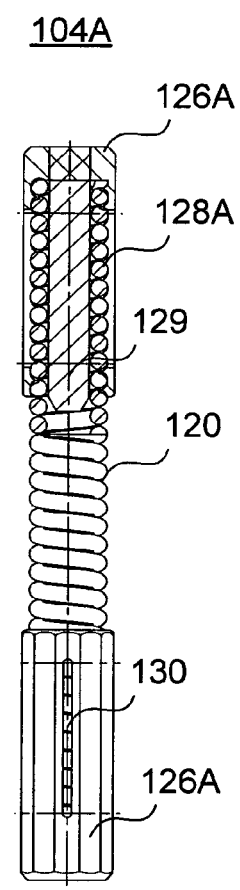

304A

FIG. 8
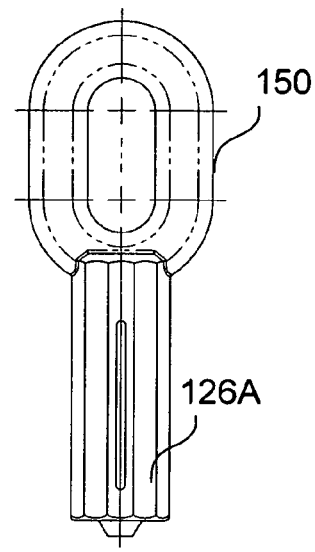
FIG. 9
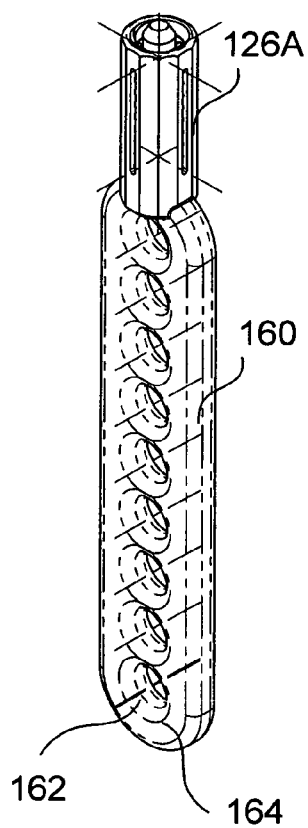
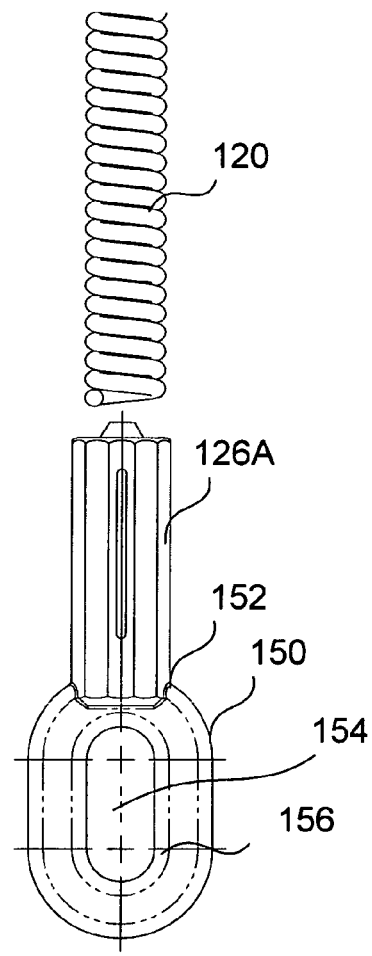

METHODS AND APPARATUS FOR VERTEBRAL STABILIZATION USING SLEEVED SPRINGS

CROSS REFERENCE TO RELATED APPLICATIONS

This application claims the benefit of U.S. Provisional Patent Application No. 60/658,365, filed Mar. 3, 2005, the entire disclosure of which is hereby incorporated by reference.

BACKGROUND OF THE INVENTION

The present invention is directed to vertebral stabilization of a spine using springs.

Back pain is one of the most common and often debilitating conditions affecting millions of people in all walks of life. Today, it is estimated that over ten million people in the United States alone suffer from persistent back pain. Approximately half of those suffering from persistent back pain are afflicted with chronic disabling pain, which seriously compromises a person's quality of life and is the second most common cause of worker absenteeism. Further, the cost of treating chronic back pain is very high, even though the majority of sufferers do not receive treatment due to health risks, limited treatment options and inadequate therapeutic results. Thus, chronic back pain has a significantly adverse effect on a person's quality of life, on industrial productivity, and on heath care expenditures.

Degenerative spinal column diseases, such as disc degenerative diseases (DDD), spinal stenosis, spondylolisthesis, and so on, need surgical operation if they do not take a turn for the better by conservative management. Typically, spinal decompression is the first surgical procedure that is performed. The primary purpose of decompression is to reduce pressure in the spinal canal and on nerve roots located therein by removing a certain tissue of the spinal column to reduce or eliminate the pressure and pain caused by the pressure. If the tissue of the spinal column is removed the pain is reduced but the spinal column is weakened. Therefore, fusion surgery (e.g., ALIF, PLIF or posterolateral fusion) is often necessary for spinal stability following the decompression procedure. However, following the surgical procedure, fusion takes additional time to achieve maximum stability and a spinal fixation device is typically used to support the spinal column until a desired level of fusion is achieved. Depending on a patient's particular circumstances and condition, a spinal fixation surgery can sometimes be performed immediately following decompression, without performing the fusion procedure. The fixation surgery is performed in most cases because it provides immediate postoperative stability and, if fusion surgery has also been performed, it provides support of the spine until sufficient fusion and stability has been achieved.

Conventional methods of spinal fixation utilize a rigid spinal fixation device to support an injured spinal part and prevent movement of the injured part. These conventional spinal fixation devices include: fixing screws configured to be inserted into the spinal pedicle or sacral of the backbone to a predetermined depth and angle, rods or plates configured to be positioned adjacent to the injured spinal part, and coupling elements for connecting and coupling the rods or plates to the fixing screws such that the injured spinal part is supported and held in a relatively fixed position by the rods or plates.

U.S. Pat. No. 6,193,720 discloses a conventional spinal fixation device, in which connection members of a rod or plate type are mounted on the upper ends of at least one or more screws inserted into the spinal pedicle or sacral of the backbone. The entire disclosure of the '720 patent is hereby incorporated by reference. The connection units, such as the rods and plates, are used to stabilize the injured part of the spinal column which has been weakened by decompression. The connection units also prevent further pain and injury to the patient by substantially restraining the movement of the spinal column. However, because the connection units prevent normal movement of the spinal column, after prolonged use, the spinal fixation device can cause ill effects, such as "junctional syndrome" (transitional syndrome) or "fusion disease" resulting in further complications and abnormalities associated with the spinal column. In particular, due to the high rigidity of the rods or plates used in conventional fixation devices, the patient's fixed joints are not allowed to move after the surgical operation, and the movement of the spinal joints located above or under the operated area is increased. Consequently, such spinal fixation devices cause decreased mobility of the patient and increased stress and instability to the spinal column joints adjacent to the operated area.

It has been reported that excessive rigid spinal fixation is not helpful to the fusion process due to load shielding caused by rigid fixation. Thus, trials using load sharing semi-rigid spinal fixation devices have been performed to eliminate this problem and assist the bone fusion process. For example, U.S. Pat. Nos. 5,672,175; and 5,540,688; and U.S. Patent Publication No. 2001/0037111 disclose dynamic spine stabilization devices having flexible designs that permit axial load translation (i.e., along the vertical axis of the spine) for bone fusion promotion. The entire disclosures of these patents/publication are hereby incorporated by reference. However, because these devices are intended for use following a bone fusion procedure, they are not well-suited for spinal fixation without fusion. Thus, in the end result, these devices do not prevent the problem of rigid fixation resulting from fusion.

To solve the above-described problems associated with rigid fixation, non-fusion technologies have been developed. The Graf band is one example of a non-fusion fixation device that is applied after decompression without bone fusion. The Graf band is composed of a polyethylene band and pedicle screws to couple the polyethylene band to the spinal vertebrae requiring stabilization. The primary purpose of the Graf band is to prevent sagittal rotation (flexion instability) of the injured spinal parts. Thus, it is effective in selected cases but is not appropriate for cases that require greater stability and fixation. See, Kanayama et al, Journal of Neurosurgery 95(1 Suppl):5-10, 2001, Markwalder & Wenger, Acta Neurochrgica 145(3):209-14.). Another non-fusion fixation device called "Dynesys" has been introduced, as disclosed in Stoll et al, European Spine Journal 11 Suppl 2:S170-8, 2002, Schmoelz et al, J of Spinal Disorder & Techniques 16(4):418-23, 2003. The Dynesys device is similar to the Graf band except it uses a polycarburethane spacer between the screws to maintain the distance between the heads of two corresponding pedicle screws and, hence, adjacent vertebrae in which the screws are fixed. Early reports by the inventors of the Dynesys device indicate it has been successful in many cases. However, it has not yet been determined whether the Dynesys device can maintain long-term stability with flexibility and durability in a controlled study. Because it has polyethylene components and interfaces, there is a risk of mechanical failure. Furthermore, due to the mechanical configuration of the device, the surgical technique required to attach the device to the spinal column is complex and complicated.

U.S. Pat. Nos. 5,672,175; 5,282,863; and 4,748,260, and U.S. Patent Publication No. 2003/0083657 disclose flexible spinal stabilization systems and methods using plastic, non-metallic rods and/or flexible elongate members. The entire disclosures of these patents/publication are hereby incorporated by reference. These devices are flexible but they are not well-suited for enduring long-term axial loading and stress. Additionally, the degree of desired flexibility versus rigidity may vary from patient to patient. The design of existing flexible fixation devices are not well suited to provide varying levels of flexibility to provide optimum results for each individual candidate. For example, U.S. Pat. No. 5,672,175 discloses a flexible spinal fixation device which utilizes a spring element made of metal alloy and/or a composite material. Additionally, compression or extension springs are coiled around the rod for the purpose of providing de-rotation forces on the vertebrae in a desired direction. However, this patent is primarily concerned with providing a spinal fixation device that permits "relative longitudinal translational sliding movement along [the] vertical axis" of the spine and neither teaches nor suggests any particular designs of connection units (e.g., rods or plates) that can provide various flexibility characteristics. Prior spring elements such as that mentioned in U.S. Pat. No. 5,672,175 typically have solid construction with a relatively small diameter in order to provide a desired level of flexibility. Because they are typically very thin to provide suitable flexibility, such prior art rods are prone to mechanical failure and have been known to break after implantation in patients.

U.S. Pat. Nos. 5,180,393; 5,672,175; 5733,284; and 6,835,205 disclose the use of flexible springs (instead of rods) for stabilizing adjacent vertebrae of a spine. The entire disclosures of these patents are hereby incorporated by reference. The means by which the springs disclosed in these patents are connected to the vertebrae are disadvantageous because they do not permit ease in changing the length of the spring. While, for example, U.S. Pat. No. 5,180,393 permits a cascade of spring elements, the resulting spring structure is not in axial alignment. Further, the length of each individual spring cannot be easily changed during the surgical procedure. Indeed, such appears to require adjustment during manufacture. Still further, the disclosed spring structures in these patents do not appear compatible with existing pedicle screws and tulip fixation designs. Thus, they each require specialized bone attachment devices.

Therefore, conventional spinal fixation devices have not provided a comprehensive and balanced solution to the problems associated with curing spinal diseases. Many of the prior devices are characterized by excessive rigidity, which leads to the problems discussed above while others, though providing some flexibility, are not well-adapted to provide varying degrees of flexibility. Additionally, existing flexible fixation devices utilize components that are not proven to provide long-term stability and durability, and are cumbersome and overly complex in terms of how they are adjusted and/or attach to the vertebral bones.

SUMMARY OF THE INVENTION

In accordance with one or more embodiments of the present invention, a stabilization element for implantation in a patient includes: a spring element including a plurality of helical coils terminating at first and second ends; and at least one sleeve including at least one threaded bore sized and shaped to thread onto the helical coils of the spring element, the at least one sleeve being operable to engage a tulip of a bone anchor. An overall length of the stabilization element is preferably adjustable by cutting off a section of the spring element.

The sleeve may include at least one slot extending from the threaded bore through to an external surface of the sleeve, and the slot may extend longitudinally at least partially along a length of the sleeve. Activation of a coupling mechanism of the tulip is operable to cause an internal diameter of the threaded bore to reduce via the at least one slot such that one or more surfaces of the threaded bore clamps to the helical coils of the spring element.

In one embodiment, the at least one sleeve includes a closed first end, where the threaded bore does not extend therethrough, and an open second end from which the threaded bore extends. Thus, one of the sleeves may be operable to cap the first end of the spring element, and another of the sleeves may be operable to cap the second end of the spring element.

The helical coils of the spring element preferably define a longitudinal hollow portion thereof. The at least one sleeve may include a post that extends from a bottom of the threaded bore and coaxially therewith, where a diameter of the post is sized and shaped to slide into the hollow portion of the spring element as the at least one sleeve is threaded thereon. Preferably, the post is operable to provide a reactive force to compressive forces imposed on the spring element by one or more surfaces of the threaded bore as the tulip clamps the sleeve.

A cross-section of the sleeve has a shape taken from the group consisting of rectangular, square, triangular, round, polygonal, any combination thereof, pentagonal, hexagonal, heptagonal, octagonal, nonagonal, decagonal, undecagonal, dodecagonal.

In accordance with one or more embodiments of the present invention, a stabilization element for implantation in a patient includes: at least one spring element including a plurality of helical coils terminating at first and second ends; and at least one intermediate sleeve including at least one threaded bore sized and shaped to thread onto the helical coils of the spring element, the at least one threaded bore opening at first and second opposing ends of the intermediate sleeve. The intermediate sleeve is preferably disposed between respective first and second ends of the at least one spring element, and the at least one sleeve is preferably operable to engage a tulip of a bone anchor.

In accordance with one or more embodiments of the present invention, a stabilization element for implantation in a patient includes: a spring element including a plurality of helical coils terminating at first and second ends; at least one sleeve including first and second opposing ends, and at least one threaded bore extending from the first end at least partially through the sleeve and being sized and shaped to thread onto the helical coils of first end of the spring element, the at least one sleeve being operable to engage a tulip of a bone anchor; and a rigid rod extending from the second end of the sleeve, the rod being sized and shaped to engage a further tulip of a further bone anchor.

In accordance with one or more embodiments of the present invention, a stabilization element for implantation in a patient includes: a spring element including a plurality of helical coils terminating at first and second ends; at least one sleeve including first and second opposing ends, and at least one threaded bore extending from the first end at least partially through the sleeve and being sized and shaped to thread onto the helical coils of first end of the spring element; and a coupling plate extending from the second end of the sleeve, the coupling plate including at least one aperture therethrough for receiving a bone screw to secure the coupling plate to a bone of the patient.

The coupling plate preferably includes at least one elongate aperture to permit adjustment of the coupling plate relative to the bone screw. Alternatively or in addition, the coupling plate may be elongate and include a series of apertures. In one or more embodiments, the coupling plate is long enough to span between adjacent vertebral bones of the patient. In one or more embodiments, the coupling plate may be operable to rigidly stabilize the adjacent vertebral bones relative to one another when one or more bone screws are used through the apertures to fix respective ends of the coupling plate the respective vertebral bones.

In accordance with one or more embodiments of the present invention, a stabilization element for implantation in a patient includes: a spring element including a plurality of helical coils terminating at first and second ends; and at least one sleeve including at least one bore sized and shaped to slide onto the helical coils of the spring element, the at least one sleeve being operable to engage a tulip of a bone anchor.

In accordance with one or more embodiments of the present invention, a tool for assembling a stabilization element for implantation in a patient includes: a body; and an aperture within the body that is sized and shaped to receive a sleeve, wherein the sleeve includes at least one threaded bore sized and shaped to thread onto helical coils of a spring element, and the body, when turned, applies torsional force to the sleeve for threading the sleeve onto the spring element.

In accordance with one or more embodiments of the present invention, a tool for assembling a stabilization element for implantation in a patient, includes: a clamp portion defining an interior surface; a pair of lever arms depending from the clamp portion, wherein the lever arms and the clamp portion cooperate to cause the interior surface of the clamp portion to collapse and grip a spring element of the stabilization element such that torsional forces may be applied to the spring element.

In accordance with one or more embodiments of the present invention, a method for implanting a stabilization element in a patient to stabilize at least two vertebral bones, includes: customizing a stabilization element by cutting a spring element thereof to a length, the spring element including a plurality of helical coils terminating at first and second ends; threading an end sleeve to at least one end of the spring element, the end sleeve including at least one threaded bore sized and shaped to thread onto the helical coils of the spring element; fixing a first bone anchor to one of the vertebral bones of the patient, the bone anchor including a coupling element at one end thereof operable to couple to the end sleeve of the stabilization element; and clamping the end sleeve of the stabilization element within the coupling element of the bone anchor to fix the end of the spring element to the vertebral bone of the patient.

Other aspects, features, advantages, etc. will become apparent to one skilled in the art when the description of the preferred embodiments of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

FIG. 2 illustrates a side view of some primary components of one of the intervertebral stabilizers of FIGS. 1A-1B in accordance with one or more embodiments of the present invention;

FIGS. 3A-3B illustrate a side exploded view, and a side assembled view (FIG. 3B including a partial cross-sectional view of FIG. 3A), respectively, of a stabilization element of the intervertebral stabilizer system of FIGS. 1A-1B or one or more further embodiments herein;

FIG. 8 illustrates a perspective view of a further alternative embodiment of a sleeve element that may be employed in an alternative intervertebral stabilizer element configuration in accordance with one or more embodiments of the present invention;

FIG. 9 illustrates a perspective view of a further alternative embodiment of a sleeve element that may be employed in an alternative intervertebral stabilizer element configuration in accordance with one or more embodiments of the present invention;

DETAILED DESCRIPTION

Figure 1A:
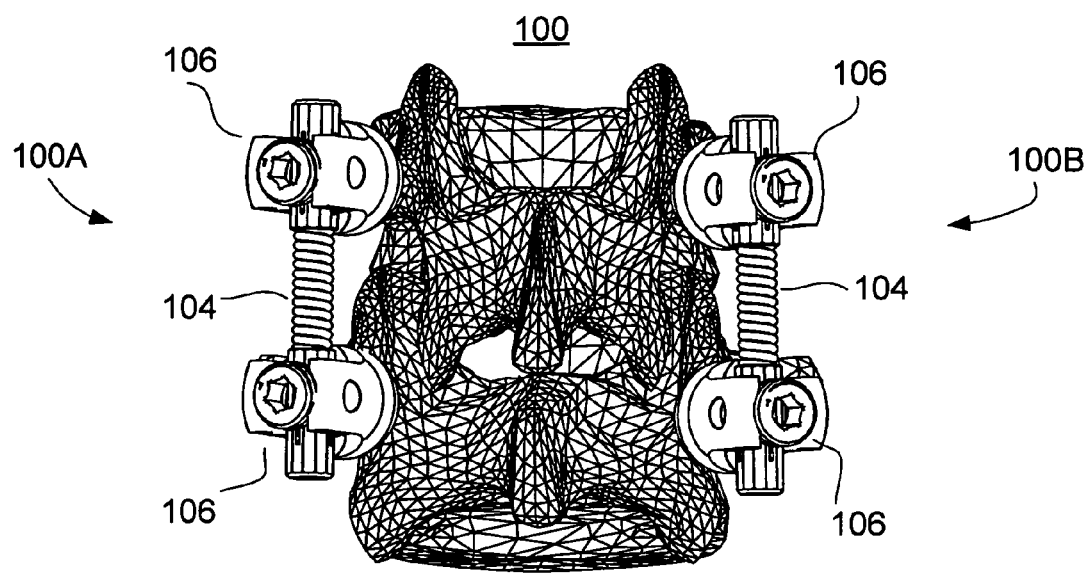
FIGS. 1A-1B illustrate posterior and side (or lateral) views, respectively, of an intervertebral stabilizer system in use in accordance with one or more embodiments of the present invention.
Figure 1B:
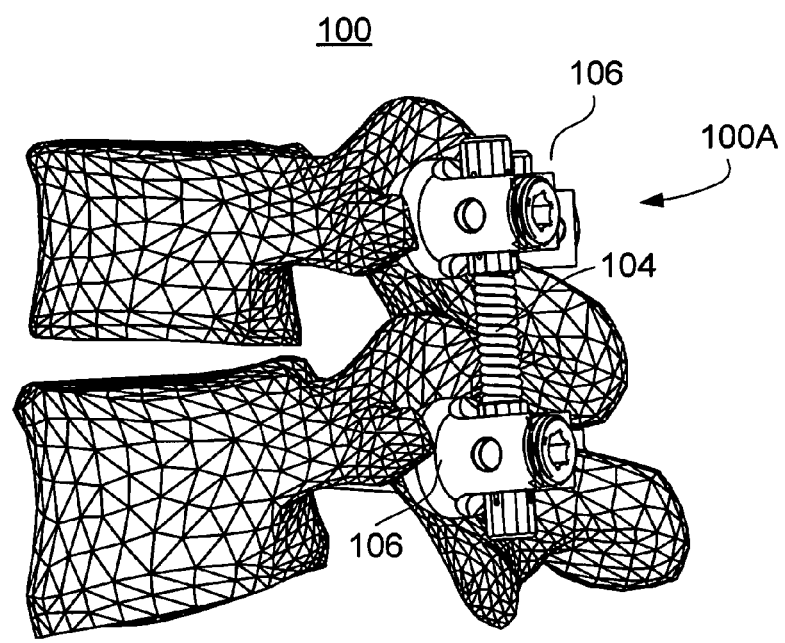

FIGS. 1A-B illustrate an embodiment of a spinal stabilizer system 100 in use in accordance with one or more aspects of the present invention. In this embodiment, the system 100 includes two stabilizing elements 100A, 100B (also referred to as dynamic stabilizers) that are designed for single level spinal stabilization, preferably from the posterior of the spine. The posterior stabilizer system 100 is preferably used at the early to moderate stages of the spinal disc degeneration disease process to inhibit posterior disc, vertebral foramen, and inferior vertebral notch collapse with the minimal (semi-constrained) restriction of the vertebral body biological range of motion.

It is understood that the use of the various embodiments of the invention discussed herein has been directed to a specific application of stabilizing the spine; however, other applications are contemplated without departing from the scope of the invention. Indeed, any application in which a spring element is called for to stabilize two anatomical bodies is within the scope of the invention.

The stabilizer system 100 is preferably sized and shaped for bilateral use on a posterior aspect of the spine. In particular, the stabilizer 100 provides stabilization with respect to adjacent vertebral bones 10, 12 of the spine. It is understood that the size and shape of the respective stabilizer elements 100A, 100B may be adapted to fit at any level of the spine, such as the cervical spine, thoracic spine, or lumbar spine. It is noted that unilateral stabilization is also contemplated and, thus, the system 100 may include a single stabilization element, for example, element 10A.

As best seen in FIG. 2, each stabilizer element 100A, 100B (element 100A being shown by way of example) includes first and second anchoring elements 102, such as pedicle screws, and a spring element 104 coupled to the screws 102. It is understood that the anchoring elements 102 need not be pedicle screws; indeed, any of the known techniques of coupling a conventional rod (e.g., a solid rod) may be employed without departing from the invention. For example, posts may be used. It is contemplated that the stabilizer system 100 may employ any pedicle screw system presently utilizing a solid fixation rod of any diameter. In this regard, the depicted embodiment employs an articulating tulip 106 coupled to each screw 102 that may be moved into various positions with respect to the screw 102. The tulips 106 are adapted to receive and clamp respective ends of the spring element 104.

In use to stabilize a portion of a spine, the anchors 102 secure the respective ends of the spring element 104 to respective portions of two adjacent vertebrae 10, 12 in order to inhibit posterior disc collapse with minimum restriction of the inter-vertebral movement. For example, the respective screws 102 may be fixed to a respective articular process of each adjacent vertebrae 10, 12, a respective transverse process of each adjacent vertebrae, a respective pedicle of each adjacent vertebrae, or other suitable respective portions of the adjacent vertebrae 10, 12.

It is most preferred that the system 100 is disposed bilaterally, where one stabilizer element 100A or 100B is disposed on each side of the spinous process and attached to respective adjacent vertebrae 10, 12 in a posterior location as discussed above. As will be discussed in further detail below, the spring element 104 preferably does not permit compression beyond a certain point at which the respective coils of the spring are in contact with one another. In one or more embodiments, no compressive movement may be allowed, i.e., when there is no distance between the respective coils of the spring and adjacent coils are in contact with one another. Thus, the dynamic stabilizers 100A, 100B located on each side of the spinous process inhibit posterior disc collapse. As the spring element 104 provides extension when tensile forces are applied, the dynamic stabilizers 100A, 100B do not substantially limit displacement, rotation, subluxation, flexion, extension, bending, or any combination thereof as between the adjacent vertebrae.

With reference to FIGS. 3A-B, the spring element 104 includes an elongate coil spring 120 having first and second ends 122, 124, respectively. The first and second ends 122, 124 are utilized as fastening zones for coupling to the respective bone anchors 102. The coil spring 120 is preferably hollow all the way through from the first end 122 to the second end 124, although alternative embodiments of the coil spring 120 may include an interrupted hollow portion therethrough.

The cross-section of the coil spring 120 may take on any shape, such as rectangular, square, triangular, hexagonal, octagonal, polygonal, or any combination thereof. It is preferred that the cross-section is round and the coil spring 120 is of a generally cylindrical configuration.

A sleeve element 126A is preferably disposed at at least one of the first end 122 and the second end 124 of the coil spring 120. The sleeve element 126A is preferably sized and shaped to engage the respective ends 122, 124 by way of threads. As best seen in FIG. 3B, the sleeve 126A preferably includes a threaded bore 128A, where the threads are preferably of a size and pitch that substantially match the size and pitch of the coils of the coil spring 120. In alternative embodiments, the threads may be of another pitch (smaller or larger), so long as the coils of the coil spring 120 conform to the pitch as the sleeve 126A is threaded onto the ends 122, 124 thereof.

In this embodiment, the sleeve 126A may function as an end cap for the coil spring 120; indeed, the threaded bore 128A does not pass completely through the sleeve 126A. Thus, the coil spring 120 may bottom out against an end surface of the threaded bore 128A.

The sleeve 126A preferably includes at least one slot 130 extending from the threaded bore 128A to a surface of the sleeve 126A and also extending along at least a portion of the length of the sleeve 126A. Thus, the ends 122, 124 (including the sleeves 126A) of the spring element 104 may be received in the respective tulips 106 of the bone anchors 102. The activation of the tulips 106 to clamp the sleeves 126A of the spring element 104 preferably applies compression forces on the sleeves 126A and causes respective internal surfaces of the threaded bores 128A to engage the respective coil springs 120.

The sleeve 126A preferably includes a post 129 that extends from the bottom of the threaded bore 128A, and preferably coaxially therewith. The post 129 is preferably sized and shaped to slide into the hollow portion of the coil spring 120 as the sleeve 126A is threaded thereon. The post 129 preferably provides a reactive force to the compressive forces imposed on the coil spring 120 by the threaded bore 128A as the respective tulip 106 clamps the sleeve 126A. Advantageously this prevents the coil spring 120 from collapsing or excessively deforming as compressive forces increase.

As seen in FIG. 2, the sleeve 126A of the spring element 120 is of a diameter suitable for reception in the tulip 106 of one of the bone anchors 102. In a preferred embodiment, the diameter of the sleeve element 126A is preferably about 5.5 mm such that widely available bone anchors 102 and tulips 106 (e.g., those designed for conventional rigid rod stabilization/fixation) may be employed to engage the sleeve element 126A without requiring specialized dimensioning of the tulip 106. Of course, other standard diameters (if any) or non-standard diameters may be employed.

The cross-section of the sleeve 126A may take on any shape, such as rectangular, square, triangular, round, polygonal, or any combination thereof. It is preferred that the cross-section is polygonal, including multi-faceted surfaces to assist in good engagement with the respective tulip 106. By way of example, the polygonal cross-section may be pentagonal, hexagonal, heptagonal, octagonal, nonagonal, decagonal, undecagonal, dodecagonal, etc. The illustrated dodecagonal cross-sectional shape is preferred.

The respective lengths of the coil spring 120 and the sleeve 126A may vary depending on the specific application of the stabilizer system 100. In the illustrated embodiment, coil spring is approximately three times as long as each of the sleeve elements 126A. In a preferred embodiment, the length of the coil spring 120 may be customized by the surgeon by cutting same to a desired length (preferably during the operating procedure so that the length may be tailored to the anatomy of the patient). Advantageously, the ability to cut the coil spring 120 to length reduces inventory while providing significant flexibility in terms of varying a length of the spring element 104 to accommodate differing anatomical conditions.

Figure 4:
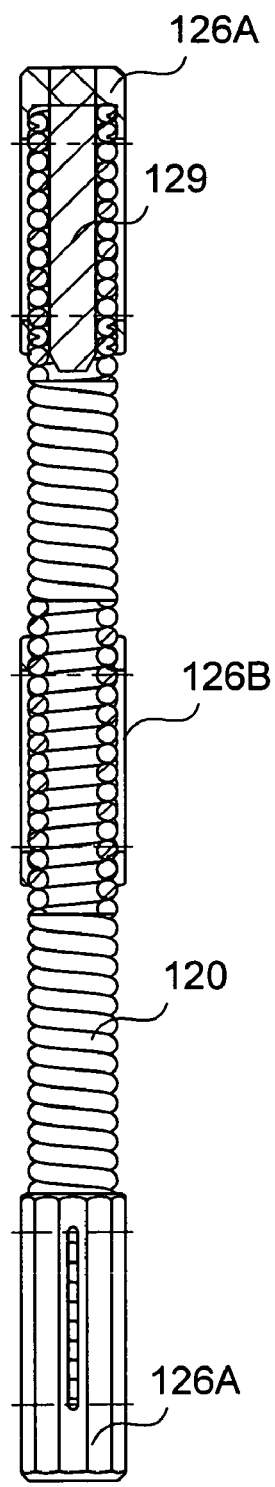
FIG. 4 illustrates a side, partially cross sectional view of a multilevel intervertebral stabilizer element in accordance with one or more further embodiments of the present invention.

It is noted that the stabilization spring element 104 may be employed in single level stabilization and/or multilevel stabilization. With reference to FIG. 4, one or more embodiments of the present invention contemplate multilevel spinal stabilization, again from the posterior of the spine. The illustrated multilevel spring element 204A of FIG. 4 includes a coil spring 120, a pair of sleeves 126A (acting as end caps), and at least one intermediate sleeve 126B. (The coil spring 120 of the multi-level embodiment illustrated in FIG. 4 would likely be substantially longer than the coil spring 120 of the single level embodiment of FIG. 3B.) For simplicity, the entirety of the bilateral (or unilateral) stabilization system employing the spring element 204A is not shown. It is sufficient to disclose to those skilled in the art that at least three bone anchors 102 (not shown) would be employed, each with a respective tulip 106, for engaging one of the sleeves 126A, 126B. As each bone anchor 102 would engage a respective vertebral bone, multi-level stabilization is obtained.

Figure 5A:
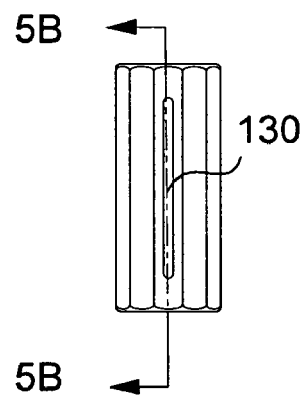
FIGS. 5A-5B illustrate a side view and a cross-sectional view, respectively, of an intermediate sleeve that may be employed with the multilevel intervertebral stabilizer element of FIG. 4 (and/or other embodiments herein)
Figure 5B:
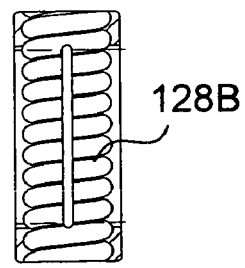

It is noted that any number of intermediate sleeves 126B may be employed to achieve stabilization of any number of vertebral levels. In the embodiment illustrated in FIG. 4, two-level stabilization is contemplated. With reference to FIGS. 4, 5A and 5B, the sleeve 126B is preferably sized and shaped to thread to an intermediate position on the coil spring 120 between the respective ends 122, 124, thereof. In this regard, the sleeve 126B preferably includes a threaded bore 128B that extends entirely through the sleeve 126B. Again, the threads are preferably of a size and pitch that substantially match the size and pitch of the coils of the coil spring 120, or cause the coils of the coil spring 120 to conform as the sleeve is threaded. Thus the coil spring 120 may be turned through the threaded bore 128B such that the sleeve 126B attains any longitudinal intermediate position along the spring 120. Advantageously, the surgeon may customize the length of the spring element 204A (e.g., by adjusting the length of the coil spring 120) and the position of the sleeve 126B thereon in order to accommodate the particularities of the patient's anatomy, such as vertebral bone positions.

The sleeve 126B also preferably includes at least one slot 130 extending from the threaded bore 128B to a surface of the sleeve 126B and also extending along at least a portion of the length of the sleeve 126B. Thus, the activation of the tulip 106 to clamp the sleeve 126B of the spring element 204A preferably applies compression forces on the sleeve 126B and causes respective internal surfaces of the threaded bore 128B to engage the coil spring 120. Like the sleeve 126A, the sleeve 126B is preferably of a diameter suitable for reception in the tulip 106 of the respective bone anchor 102, such as about 5.5 mm to avoid the need for specialized tulip designs—although any diameter may also be employed. The cross-section of the sleeve 126B may also take on any shape, such as rectangular, square, triangular, round, polygonal, or any combination thereof, although, like the sleeve 126A, the cross-section is preferably polygonal, such as dodecagonal.

Although not shown in FIG. 4, an alternative embodiment contemplates the use of a pair of coil springs 120 coupled together at a single sleeve element 126B. For example, one coil spring 120 is threaded into one end of the threaded bore 128B and the other coil spring 120 is threaded into the opposite end of the threaded bore 128B. The respective coil springs 120 may bottom out against one another, preferably near a central position within the threaded bore 128B.

Figure 6B:
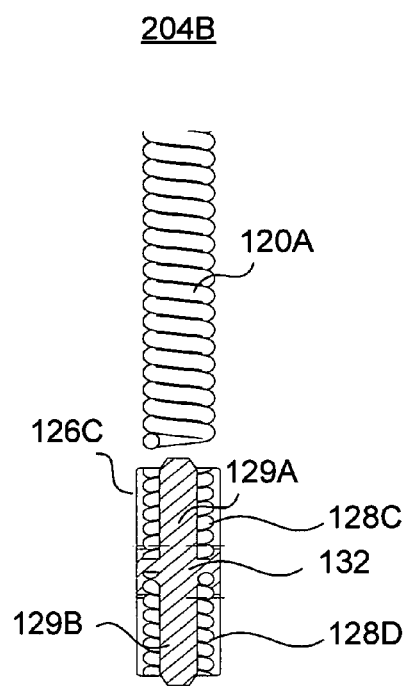
FIGS. 6A-6C illustrate a perspective view and a cross-sectional view, respectively, of alternative intermediate sleeves that may be employed with the multilevel intervertebral stabilizer element of FIG. 4 (and/or other embodiments herein)
Figure 6A:
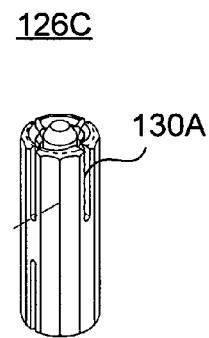

With reference to FIGS. 6A-6B, an alternative spring element 204B may be employed to achieve multilevel stabilization. The spring element 204B uses one or more intermediate sleeves 126C as opposed to the intermediate sleeve(s) 126B. In the embodiment illustrated, one intermediate sleeve 126C is employed for two-level stabilization. The intermediate sleeve 126C includes a pair of oppositely directed threaded bores 128C, 128D. The respective bores 128C, 128D extend from an intermediately disposed separation element, such as a wall 132. As with the other sleeve embodiments, the threads are preferably of a size and pitch that substantially match the size and pitch of the coils of the coil spring 120, or cause the coils of the coil spring 120 to conform as the sleeve is threaded. A pair of coil springs 120 is preferably employed, one coil spring 120A being threaded into the threaded bore 128C and the other coil spring 120D being threaded into the threaded bore 128D. The respective coil springs 120A, 120B may bottom out against the opposing end surfaces of the wall 132.

The sleeve 126C also preferably includes at least one slot 130A extending from at least one (and preferably both) of the threaded bore 128C, 128D to a surface of the sleeve 126C. As best seen in FIG. 6A, it is preferred that a plurality of such slots 130A extend along the length of the sleeve 126C, toward respective ends thereof. Thus, the activation of the respective tulip 106 (not shown) to clamp the sleeve 126C of the spring element 204BA preferably applies compression forces on the sleeve 126C and causes respective internal surfaces of the threaded bores 128C, 128D to engage the coil springs 120A, 120B.

Similar to the sleeve 126A, the sleeve 126C preferably includes at least one post 129 that extends from the wall 132 of one or both of the threaded bores 128C, 128D. The post 129 preferably extends coaxially within the threaded bore 128C and/or 128D. It is most preferred that respective posts 129A, 129B extend from respective sides of the wall 132, coaxially within the respective threaded bores 128C, 128D. Each post 129A, 129B is preferably sized and shaped to slide into the hollow portion of the associated coil spring 120A, 120B as the sleeve 126C is threaded thereon. Again, each post 129 preferably provides a reactive force to the compressive forces imposed on the coil springs 120A, 120B by the threaded bores 128C, 128D as the tulip 106 clamps the sleeve 126C.

Like the other sleeve embodiments, the sleeve 126C is preferably of a diameter suitable for reception in the tulip 106 of the respective bone anchor 102, such as about 5.5 mm to avoid the need for specialized tulip designs—although any diameter may also be employed. The cross-section of the sleeve 126C may also take on any shape, such as rectangular, square, triangular, round, polygonal, or any combination thereof, although, like the sleeve 126A, the cross-section is preferably polygonal, such as dodecagonal.

Additional levels of stabilization may be achieved by cascading respective coil springs 120 using one or more of the intermediate sleeves 126C.

Figure 6C:
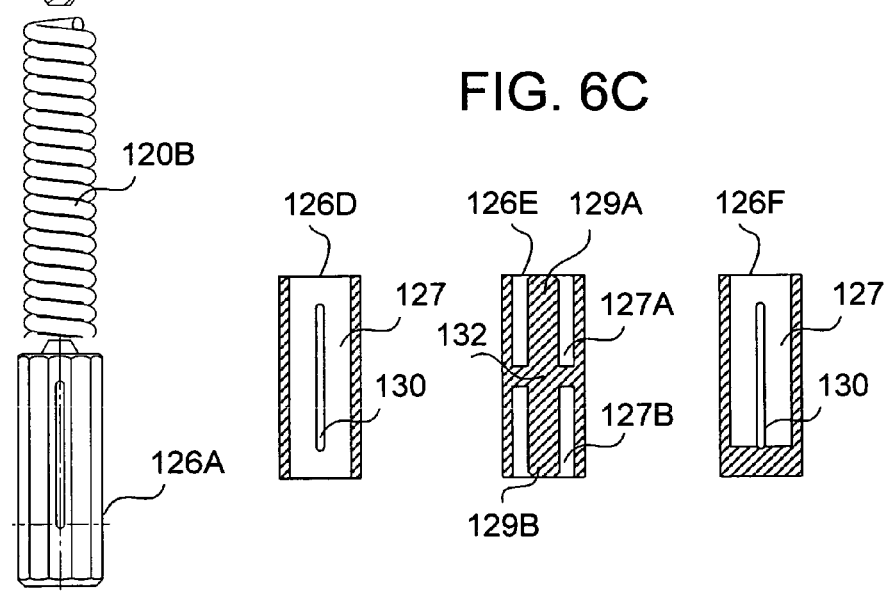

With reference to FIG. 6C, alternative intermediate sleeves 126D and 126E, and alternative end sleeve 126F are illustrated. Any of the intermediate sleeves and/or end sleeves of the embodiments herein may be substituted with the sleeves of FIG. 6C in accordance with further aspects of the present invention. The sleeves 126D, 126E, and 126F include non-threaded (e.g., smooth or rough) bores 127 as opposed to the threaded bores 128 of the other embodiments herein. While the intermediate sleeve 126D includes a through bore 127, the intermediate sleeve 126E includes respective bores 127A, 127B extending from a central wall 132. The bores 127 are preferably of a size that substantially matches the size of the coils of the coil spring 120, or cause the coils of the coil spring 120 to conform as the sleeve is pressed or slid onto the coil spring 120. In a multi-level application, the respective coil springs 120A, 120B may bottom out against one another (if sleeve 126D is employed) or against the opposing end surfaces of the wall 132 (if sleeve 126E is employed).

The sleeve 126D, 126E, and 126F also preferably includes at least one slot 130 extending from at least one (and preferably both) of the bore 127 to a surface of the sleeve 126. It is preferred that a plurality of such slots 130 extend along the length of the sleeve 126, toward respective ends thereof. Thus, the activation of the respective tulip 106 (not shown) to clamp the sleeve 126 of the spring element (e.g., similar to spring element 204B) preferably applies compression forces on the sleeves 126 and causes respective internal surfaces of the bores 127 to engage the coil springs 120A, 120B.

Similar to the sleeve 126A, the sleeve 126E preferably includes at least one post 129 that extends from the wall 132 of one or both of the bores 127A, 127B. The post 129 preferably extends coaxially within the bore 127A and/or 127B. It is most preferred that respective posts 129A, 129B extend from respective sides of the wall 132, coaxially within the respective bores 127A, 127B. Each post 129A, 129B is preferably sized and shaped to slide into the hollow portion of the associated coil spring 120A, 120B as the sleeve 126E is slid thereon. Again, each post 129 preferably provides a reactive force to the compressive forces imposed on the coil springs 120A, 120B by the bores 127A, 127B as the tulip 106 clamps the sleeve 126E.

Figure 7:
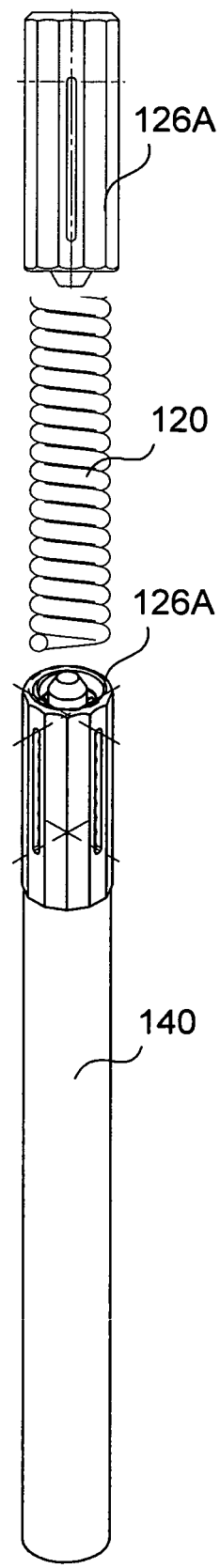
FIG. 7 illustrates a perspective view of a further alternative embodiment of a sleeve element that may be employed in an alternative multilevel intervertebral stabilizer element configuration in accordance with one or more embodiments of the present invention.

With reference to FIG. 7, one or more embodiments of the present invention may employ a spring element 304A, which includes a combination of a sleeve element 126A and a relatively rigid rod 140 (such as a solid rod). Although use of the sleeve element 126A embodiment is preferred, any of the other sleeve element embodiments may also be employed. Multilevel stabilization may be readily achieved by threading a coil spring 120 into the sleeve element 126A. The resulting spring element 304A includes a rigid section (via the rod 140) and a flexible section (via the coil spring 120). The rod 140 may provide a rigid stabilization at one or more levels (dependent on the length of the rod 140), while the coil spring 120 may provide dynamic stabilization at the next level (and/or subsequent levels depending on the length of the coil spring 120). Additional levels of stabilization may be achieved by cascading respective coil springs 120 and/or rods 140 using one or more of the sleeve embodiments described herein.

With reference to FIG. 8, one or more embodiments of the present invention may employ a spring element 404A, which includes one or more sleeve elements 126A, one or more coupling plates 150, and at least one coil spring 120. The coupling plate 150 is connected, at an end 152 thereof, to an end of a sleeve element, such as the sleeve element 126A. Although use of the sleeve element 126A embodiment is preferred, any of the other sleeve element embodiments may also be employed. The plate 150 includes an aperture 154 therethrough for receiving a bone screw (not shown). The aperture is preferably elongate to permit some adjustment in the position of the plate 150 relative to the bone screw. Preferably a conventional bone screw is employed that includes a beveled head to engage a chamfer 156 of the aperture 154. The bone screw is operable to fix the sleeve 126A and one end of the spring element 404A to the vertebral bone. Another bone screw may be used to fix the other coupling plate 150 of the spring element 404A to an adjacent vertebral bone. The illustrated embodiment of the spring element 404A is for single level stabilization. Multilevel stabilization may readily be achieved using one or more intermediate sleeves (e.g., sleeves 126B, 126C) and one or more coil springs 120 and/or rods 140.

With reference to FIG. 9, the spring element 404A may employ a coupling plate 160 as an alternative to the coupling plate 150 of FIG. 8. The coupling plate 160 includes a plurality of apertures 162 disposed in a linear arrangement therealong. The surgeon may select one or more of the apertures 162 for use in securing the coupling plate 160 to the vertebral bone based on the anatomy of the patient. A conventional bone screw is preferably employed (which may include a beveled head) to engage a chamfer 164 of the aperture 162 and secure the plate 160 to the bone. If desired, the surgeon may cut the coupling plate 160 to a custom size for the patient. Similar to the discussion of the spring element 404A of FIG. 8, if the spring element 404A employs one or more coupling plates 160, single level stabilization or multilevel stabilization may be achieved using the appropriate sleeves, coil springs, and/or rods. Notably, the coupling plate 160 may be used for rigid stabilization of a level by using same to span an intervertebral space. The coupling plate 160 may be fastened to adjacent vertebral bones by way of apertures 162 on either end of the plate 160.

Figure 10:
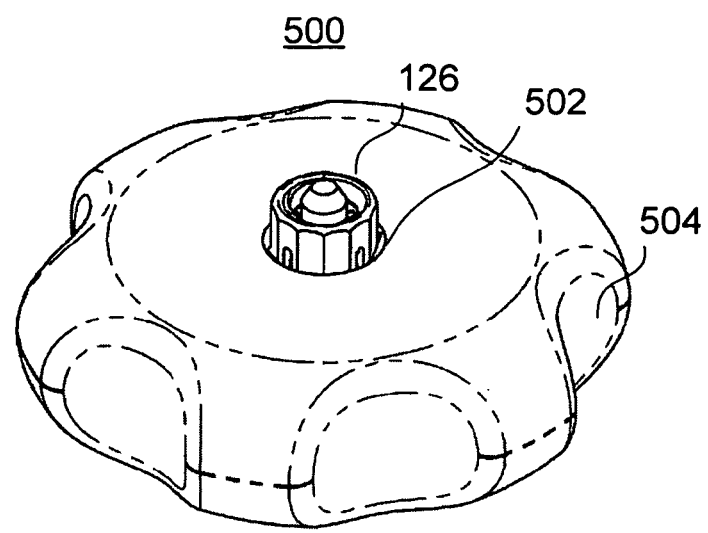
FIG. 10 illustrates a perspective view of an assembly device for use in holding a sleeve element when the sleeve element is coupled to a spring element in accordance with one or more embodiments of the present invention.
Figure 11:
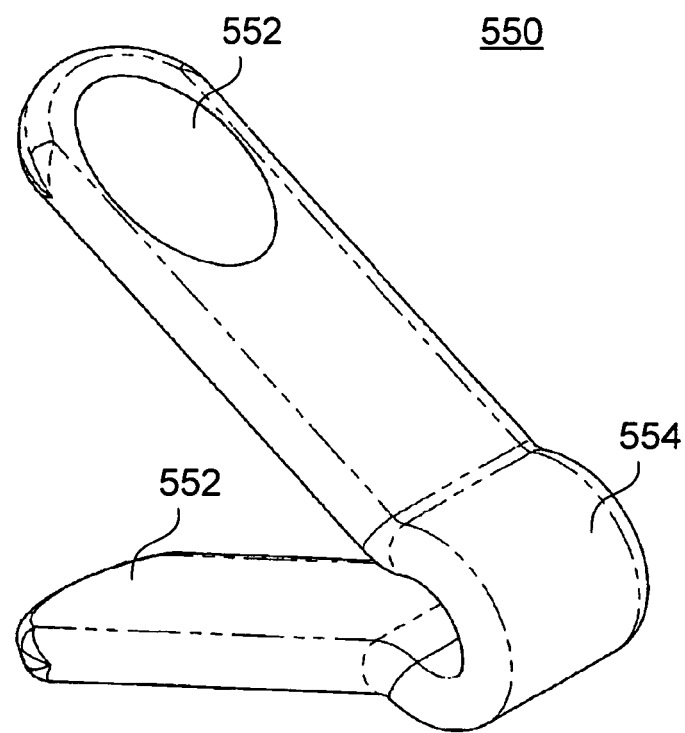
FIG. 11 illustrates a perspective view of an assembly device for use in holding a spring element when a sleeve element is coupled to the spring element in accordance with one or more embodiments of the present invention.

With reference to FIGS. 10 and 11, one or more assembly tools may be made available to the surgeon when implanting one or more of the stabilizing elements discussed above. For example, the spring element 204A (FIG. 4) may be assembled using the sleeve wrench 500 of FIG. 10 and the spring holder 550 of FIG. 11. In particular, the sleeve wrench includes a central aperture 502 sized and shaped to slideably receive a sleeve 126 (which may be any of the sleeve embodiments herein). The aperture 502 preferably includes a faceted inner surface that complements the contour of the sleeve 126. For example, if the sleeve 126 is of polygonal contour, the aperture 502 of the wrench 500 preferably includes a corresponding contour, although it need not be of exactly the same contour as the sleeve 126. The overall shape of the wrench 500 is preferably of generally flat-circular construction such that the surgeon (or an assistant) may easily grasp same and turn the sleeve 126 onto the coil spring 120. Preferably, the wrench 500 includes a plurality of relief cuts or impressions 504 to assist in grasping same. The wrench 500 may alternatively or additionally include knurling or the like.

The spring holder 550 is preferably operable to clamp the coil spring 120 such that it does not turn when the sleeve 126 is being threaded thereon. In particular, the spring holder 550 preferably includes a pair of actuators 552, such as in the form of lever arms that communicate with a clamp element 554. The coil spring 120 is preferably slid into or otherwise placed into the clamp element 554. As the actuators 552 are pressed toward one another, an interior surface of the clamp element 554 collapses, thereby gripping the coil spring 120.

Preferably the components discussed above are formed from CP Titanium or Titanium Alloy, Stainless Steel, Cobalt Chromium Alloy, Plastics and/or other biologically acceptable materials. The tools of FIGS. 10 and 11 may be formed from non-biologically acceptable materials, such as steel. The portions of the device may be produced in the range of sizes and length adequate to the requirements.

Some notable features of the aforementioned stabilizers are listed below, it being understood that various features alone or in combination may be employed:
  posterior disc collapse inhibited with minimal restriction of the vertebral body biological ROM;
  minimum pre-determined distance between bone anchors (or any attachment points) maintained without limiting displacement, rotation, subluxation, flexion, extension, bending or any combination thereof;
  locking mechanism accommodating any existing screw system presently used for solid rod fixation;

hybrid multilevel system configurations permitted;
controlled system flexibility permitted;
cross-section can be circular, square, rectangular, polygonal and any combination thereof; and
rigidity in specific direction controlled.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A stabilization element for implantation in a patient, comprising:
   a spring element including a plurality of helical coils terminating at first and second ends; and
   at least one sleeve, including: (i) a closed first end, (ii) an open second end, (iii) at least one threaded bore extending from the open second end of the at least one sleeve and being sized and shaped to thread onto the helical coils of the spring element, and (iv) at least one slot extending from the threaded bore through to an external surface of the sleeve, extending longitudinally at least partially along a length of the sleeve,
   wherein the at least one sleeve is operable to engage a tulip of a bone anchor, and to only cap at least one of the first end and the second end of the spring element.

2. The stabilization element of claim 1, wherein activation of a coupling mechanism of the tulip is operable to cause an internal diameter of the threaded bore to reduce via the at least one slot such that one or more surfaces of the threaded bore clamps to the helical coils of the spring element.

3. The stabilization element of claim 1, wherein at least one of:
   one of the sleeves is operable to cap the first end of the spring element; and
   another of the sleeves is operable to cap the second end of the spring element.

4. The stabilization element of claim 1, wherein:
   the helical coils of the spring element define a longitudinal hollow portion thereof;
   the at least one sleeve includes a post that extends from a bottom of the threaded bore and coaxially therewith; and
   a diameter of the post is sized and shaped to slide into the hollow portion of the spring element as the at least one sleeve is threaded thereon.

5. The stabilization element of claim 4, wherein the post is operable to provide a reactive force to compressive forces imposed on the spring element by one or more surfaces of the threaded bore as the tulip clamps the sleeve.

6. The stabilization element of claim 1, wherein a cross-section of the sleeve has a shape taken from the group consisting of rectangular, square, triangular, round, polygonal, any combination thereof, pentagonal, hexagonal, heptagonal, octagonal, nonagonal, decagonal, undecagonal, dodecagonal.

7. The stabilization element of claim 1, wherein an overall length of the stabilization element is adjustable by cutting off a section of the spring element.

8. A stabilization element for implantation in a patient, comprising:
   a spring element including a plurality of helical coils terminating at first and second ends;
   at least one sleeve, including: (i) an open first end, (ii) a closed second end, where the open first end and the closed second end of the at least one sleeve oppose each other, (iii) at least one threaded bore extending from the open first end of the at least one sleeve at least partially through the sleeve and being sized and shaped to thread onto the helical coils of the spring element, and (iv) at least one slot extending from the threaded bore through to an external surface of the sleeve, extending longitudinally at least partially along a length of the sleeve, wherein the at least one sleeve is operable to engage a tulip of a bone anchor, and to only cap at least one of the first end and the second end of the spring element; and
   a rigid rod extending from the closed second end of the sleeve, the rod being sized and shaped to engage a further tulip of a further bone anchor.

9. The stabilization element of claim 8, further comprising:
   an end sleeve including a closed end and an open end from which a threaded bore extends into the end sleeve, which threaded bore is sized and shaped to at least one of: thread onto the helical coils of the second end of the spring element when the at least one sleeve is threaded onto the helical coils of the first end of the spring element; and thread onto the helical coils of the first end of the spring element when the at least one sleeve is threaded onto the helical coils of the second end of the spring element.

10. A stabilization element for implantation in a patient, comprising:
    a spring element including a plurality of helical coils terminating at first and second ends;
    at least one sleeve, including: (i) an open first end, (ii) a closed second end, where the open first end and the closed second end of the at least one sleeve oppose each other, (iii) at least one threaded bore extending from the open first end of the at least one sleeve at least partially through the sleeve and being sized and shaped to thread onto the helical coils of the spring element, and (iv) at least one slot extending from the threaded bore through to an external surface of the sleeve, extending longitudinally at least partially along a length of the sleeve, wherein the at least one sleeve is operable to engage a tulip of a bone anchor, and to only cap at least one of the first end and the second end of the spring element; and
    a coupling plate extending from the second end of the sleeve, the coupling plate including at least one aperture therethrough for receiving a bone screw to secure the coupling plate to a bone of the patient.

11. The stabilization element of claim 10, wherein the coupling plate includes at least one elongate aperture to permit adjustment of the coupling plate relative to the bone screw.

12. The stabilization element of claim 10, wherein the coupling plate is elongate and includes a series of apertures.

13. The stabilization element of claim 12, wherein the coupling plate is long enough to span between adjacent vertebral bones of the patient.

14. The stabilization element of claim 13, wherein the coupling plate is operable to rigidly stabilize the adjacent vertebral bones relative to one another when one or more bone screws are used through the apertures to fix respective ends of the coupling plate the respective vertebral bones.

15. A system for stabilizing a plurality of bones of a patient, comprising:
    a first stabilization element including: a spring element including a plurality of helical coils terminating at first and second ends; and at least two sleeves, each including: (i) a closed first end, (ii) an open second end, (iii) at least one threaded bore extending from the open second end and being sized and shaped to thread onto the helical coils of the spring element, and (iv) at least one slot extending from the threaded bore through to an external surface of the respective sleeve, extending longitudinally at least partially along a length of the respective sleeve, wherein the at least two sleeves are each operable to engage a tulip of a bone anchor, and to only cap at least one of the first end and the second end of the spring element;

a first bone anchor operable to fixedly connect to one of the bones of the patient, and including a first coupling element at one end thereof operable to couple to one of the sleeves of the first stabilization element; and a second bone anchor operable to fixedly connect to another of the bones of the patient, and including a second coupling element at one end thereof operable to couple to the other of the sleeves of the first stabilization element.

16. A method of implanting a stabilization element in a patient to stabilize at least two vertebral bones, comprising:

customizing a stabilization element by cutting a spring element thereof to a length, the spring element including a plurality of helical coils terminating at first and second ends;

threading at least one end sleeve to at least one of the first end and the second end of the spring element, the at least one end sleeve including: (i) a closed first end, (ii) an open second end, (iii) at least one threaded bore extending from the open second end and being sized and shaped to thread onto the helical coils of the spring element, and (iv) at least one slot extending from the threaded bore through to an external surface of the end sleeve, extending longitudinally at least partially along a length of the end sleeve, wherein the at least one end sleeve is operable to engage a tulip of a bone anchor, and to only cap at least one of the first end and the second end of the spring element;

fixing a first bone anchor to one of the vertebral bones of the patient, the bone anchor including a coupling element at one end thereof operable to couple to the end sleeve of the stabilization element; and clamping the end sleeve of the stabilization element within the coupling element of the bone anchor to fix the end of the spring element to the vertebral bone of the patient.

* * * * *